US00PP15444P2

(12) United States Plant Patent
Lamb et al.

(10) Patent No.: US PP15,444 P2
(45) Date of Patent: Dec. 21, 2004

(54) ***ANTHURIUM* PLANT NAMED 'PATRIOT'**

(50) Latin Name: *Anthurium×hybrid*
Varietal Denomination: Patriot

(75) Inventors: Ann E. Lamb, Sebring, FL (US); Marianne E. Knauss, Longwood, FL (US)

(73) Assignee: Twyford International, Inc., Apopka, FL (US)

( * ) Notice: Subject to any disclaimer, the term of this patent is extended or adjusted under 35 U.S.C. 154(b) by 0 days.

(21) Appl. No.: 10/770,217

(22) Filed: Feb. 2, 2004

(51) Int. Cl.[7] ..... A01H 5/00

(52) U.S. Cl. ..... Plt./365

(58) Field of Search ..... Plt./365

*Primary Examiner*—Bruce R. Campell
*Assistant Examiner*—W C Haas
(74) *Attorney, Agent, or Firm*—C. A. Whealy

(57) ABSTRACT

A new and distinct cultivar of *Anthurium* plant named 'Patriot', characterized by its upright and outwardly spreading plant habit; relatively intermediate in size; glossy dark green-colored leaves with reddish brown-colored venation and petioles; ovate-shaped, dark red-colored spathes with whitish-colored spadices; inflorescences that are positioned above the foliage on strong and erect reddish brown-colored scapes; and excellent inflorescence longevity with spathes maintaining dark red coloration for at least eight weeks.

2 Drawing Sheets

Botanical classification/cultivar designation: *Anthurium× hybrid* cultivar Patriot.

BACKGROUND OF THE INVENTION

The present invention relates to a new and distinct cultivar of *Anthurium* plant, botanically known as *Anthurium× hybrid,* and hereinafter referred to by the cultivar name 'Patriot'.

The new *Anthurium* is a product of a planned breeding program conducted by the Inventors in Apopka, Fla. The objective of the breeding program is to create new *Anthurium* cultivars with dark red-colored spathes, dark green-colored foliage and a uniform and freely flowering habit.

The new *Anthurium* originated from a cross-pollination made by the Inventors in Apopka, Fla. in September, 2000, of the *Anthurium×hybrid* cultivar Cherry Red, disclosed in U.S. Plant Pat. No. 12,315, as the female, or seed, parent with a proprietary selection of *Anthurium×hybrid* identified as code number 167-1, not patented, as the male, or pollen, parent. The cultivar Patriot was discovered and selected by the Inventors as a flowering plant within the progeny of the stated cross-pollination in a controlled environment in Apopka, Fla., in August, 2002.

Asexual reproduction of the new cultivar by meristem culture in a controlled environment in Sebring, Fla., since 2002, has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Patriot. These characteristics in combination distinguish 'Patriot' as a new and distinct cultivar of *Anthurium*:

1. Upright and outwardly spreading plant habit; relatively intermediate in size.
2. Glossy dark green-colored leaves with reddish brown-colored venation and petioles.
3. Ovate-shaped, dark red-colored spathes with whitish-colored spadices.
4. Inflorescences that are positioned above the foliage on strong and erect reddish brown-colored scapes.
5. Excellent inflorescence longevity with spathes maintaining dark red coloration for at least eight weeks.

Plants of the new *Anthurium* are most similar to plants of the female parent, the cultivar Cherry Red. In side-by-side comparisons conducted in Apopka, Fla., plants of the new *Anthurium* differed from plants of the cultivar Cherry Red in the following characteristics:

1. Plants of the new *Anthurium* were more compact and better suited to smaller container sizes than plants of the cultivar Cherry Red.
2. Leaves of plants of the new *Anthurium* were smaller and narrower than leaves of plants of the cultivar Cherry Red.
3. Spathes of plants of the new *Anthurium* were smaller and more rounded in shape than spathes of plants of the cultivar Cherry Red.

Plants of the new *Anthurium* can be compared to plants of the male parent, the proprietary selection identified as code number 167-1. In side-by-side comparisons conducted in Apopka, Fla., plants of the new *Anthurium* differed from plants of the male parent selection in the following characteristics:

1. Leaves of plants of the new *Anthurium* were narrower and darker green in color than leaves of plants of the male parent selection.
2. Leaf venation, petioles and scapes of plants of the new *Anthurium* were reddish brown in color whereas leaf venation, petioles and scapes of plants of the male parent selection were green in color.

3. Spathes of plants of the new *Anthurium* were dark red in color whereas spathes of plants of the male parent selection were lavender in color.

BRIEF DESCRIPTION OF THE PHOTOGRAPHS

The accompanying colored photographs illustrate the overall appearance of the new *Anthurium*, showing the colors as true as it is reasonably possible to obtain in colored reproductions of this type. Colors in the photographs may differ slightly from the color values cited in the detailed botanical description which accurately describe the colors of the new *Anthurium*.

The photograph on the first sheet comprises a side perspective view of a typical 14-month old flowering plant of the cultivar Patriot grown in a 15-cm container.

The photograph on the second sheet is a close-up view of typical leaves and inflorescences of the cultivar Patriot.

DETAILED BOTANICAL DESCRIPTION

The following observations and measurements describe 14-month old plants grown in 15-cm containers in Apopka, Fla., in a polyethylene-covered greenhouse with day temperatures ranging from 24 to 35° C., night temperatures ranging from 18 to 24° C., and light levels about 1,500 foot-candles.

In the following description, color references are made to The Royal Horticultural Society Colour Chart, 1995 Edition, except where general terms of ordinary dictionary significance are used.

Botanical classification: *Anthurium×hybrid* cultivar Patriot.

Parentage:

*Female, or seed, parent.*—*Anthurium×hybrid* Cherry Red, disclosed in U.S. Plant Pat. No. 12,315.

*Male, or pollen, parent.*—Proprietary selection of *Anthurium×hybrid* identified as code number 167-1, not patented.

Propagation:

*Type.*—Asexual; by meristem culture.

*Time to initiate roots on a meristem-cultured plant.*—Summer: About two weeks at temperatures of 26° C. Winter: About three weeks at temperatures of 21° C.

*Time to produce a rooted meristem-cultured young plant.*—Summer: About 14 weeks at temperatures of 26° C. Winter: About 16 weeks at temperatures of 21° C.

*Root description.*—White-colored thick fleshy roots with fine lateral roots; root tip, 146D in color.

Plant description:

*Plant shape.*—Upright and outwardly spreading plant habit, inverted triangle, symmetrical; relatively intermediate in size.

*Growth habit.*—Freely clumping, bushy and dense growth habit.

*Plant height, soil level to top of leaf canopy.*—About 40 to 48 cm.

*Plant diameter or spread.*—About 60 to 70 cm.

*Foliage description.*—Length: About 19 to 22 mm. Width: About 10 to 13 cm. Shape: Deltoid. Apex: Acuminate to apiculate. Base: Truncate to somewhat cordate. Margin: Entire; somewhat undulate. Texture, upper and lower surfaces: Leathery; glabrous, smooth. Luster, upper and lower surfaces: Glossy. Venation: Midvein with well-defined primary veins radiating out from the petiole junction. Midvein protrudes from the upper surface for about 75% of the leaf length. Primary veins protrude on the lower surface. Typically about four to six primary veins per leaf. Petiole: Length: About 24 to 30 cm. Diameter, just below the geniculum: About 4 mm. Geniculum: Length: About 3 cm. Diameter: About 4 mm. Orientation: Typically curved. Petiole sheath: Length: About 3.5 cm. Width, at midpoint: About 5 mm. Apex: Rounded. Cataphyll: New leaves emerge from a cataphyll which turns brown with development and eventually abscises. Length: About 5 to 12 cm. Width, at base: About 3 cm. Shape: Triangular. Apex: Acute to apiculate. Margin: Entire. Texture, upper and lower surfaces: Smooth. Color: Developing leaves, upper surface: Darker than but closest to 137B. Developing leaves, lower surface: 147B. Fully expanded leaves, upper surface: Much darker and more green than but closest to 137A. Fully expanded leaves, lower surface: Darker and more green than but closest to 147B. Midrib, developing leaves, upper surface: 146C. Midrib, developing leaves, lower surface: 145A. Midrib, fully expanded leaves, upper surface: 166A. Midrib, fully expanded leaves, lower surface: 146B. Petiole: Darker and more red than but closest to 166A, towards the base, flushed with 146B. Geniculum: 146C, flushed with 166A. Petiole sheath: 146C. Cataphyll, upper surface: 146B. Cataphyll, lower surface: 146B, towards the apex, flushed with 177A.

Inflorescence description:

*Inflorescence arrangement.*—When developing, the spathe is tightly rolled around the spadix and emerges from the petiole sheath. The spathe is fully opened approximately when the scape is fully elongated; spathes open vertically. Spathes with spadices held above the foliage on strong, straight, wiry scapes. Inflorescences are typically grouped towards the center of the plant. Freely and continuous flowering year-round; about ten open inflorescences and about two flower buds per plant at one time.

*Inflorescence longevity.*—Inflorescences maintain good color and substance on the plant for at least eight weeks. As cut flowers, inflorescences maintain good color and substance for about two to three weeks. Inflorescences persistent.

*Time to flower.*—First flowers develop about seven months after planting 20-week old rooted young plants.

*Spathe.*—Length: About 9 to 11.5 cm. Width: About 5.6 cm. Shape: Ovate. Apex: Acute, terminated by a straight apicula. Base: Cordate. Margin: Entire. Texture, upper and lower surfaces: Leathery; glabrous, smooth. Aspect: Initially cupped, flattening somewhat with development. Color: When opening and fully opened, front surface: 46A, color becoming closer to 187A tinged with 46A with development; apicula, 146A. When opening and fully opened, back surface: 46A tinged with 53A, color becoming closer to 53A tinged with 46A with development; apicula, 146A.

*Spadix.*—Length: About 5 to 6.6 cm. Diameter: About 7.5 mm. Shape: Columnar. Cross section: Rounded. Longitudinal axis: Erect. Color: When the spathe unrolls, the spadix is closest to but lighter than 155A, towards the apex, 4D. When the spathe is fully open the spadix becomes closer to 47B with 144A towards the apex.

*Reproductive organs.*—Androecium: Anthers and filaments are minute and not clearly visible. Pollen, white in color, closest to 155D. Gynoecium: Pistils are translucent white and protrude between the staminate flowers and extend about 0.5 mm beyond the stamens.

*Scape.*—Length: About 45 to 50 cm. Aspect: Strong and erect, wiry. Color: Darker and more red than but closest to 166A.

*Fruit.*—Shape: Oblong to elliptic. Length: About 4 mm. Diameter: About 3 mm. Color: 145C; flesh, translucent yellow/orange, 22D.

*Seed.*—Quantity per fruit: One or two. Quantity per inflorescence: About 80 to 120. Shape: Elliptic, often somewhat flattened. Length: About 2 mm. Diameter: About 1.5 mm. Color: 145B.

Disease/pest resistance: Under commercial conditions, plants of the new *Anthurium* have not been observed to be resistant to pathogens or pests common to *Anthurium*.

Temperature tolerance: Plants of the new *Anthurium* have been observed to be tolerant to temperatures ranging from 10 to 39° C.

It is claimed:

1. A new and distinct cultivar of *Anthurium* plant named 'Patriot', as illustrated and described.

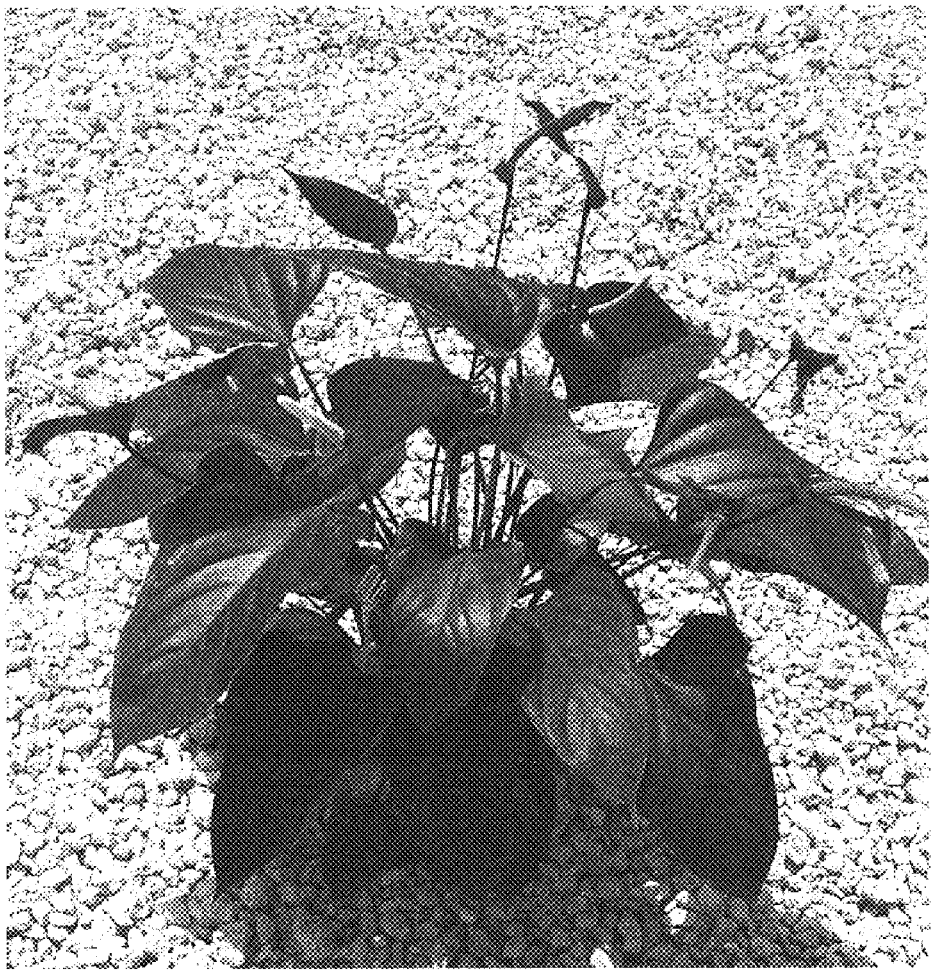

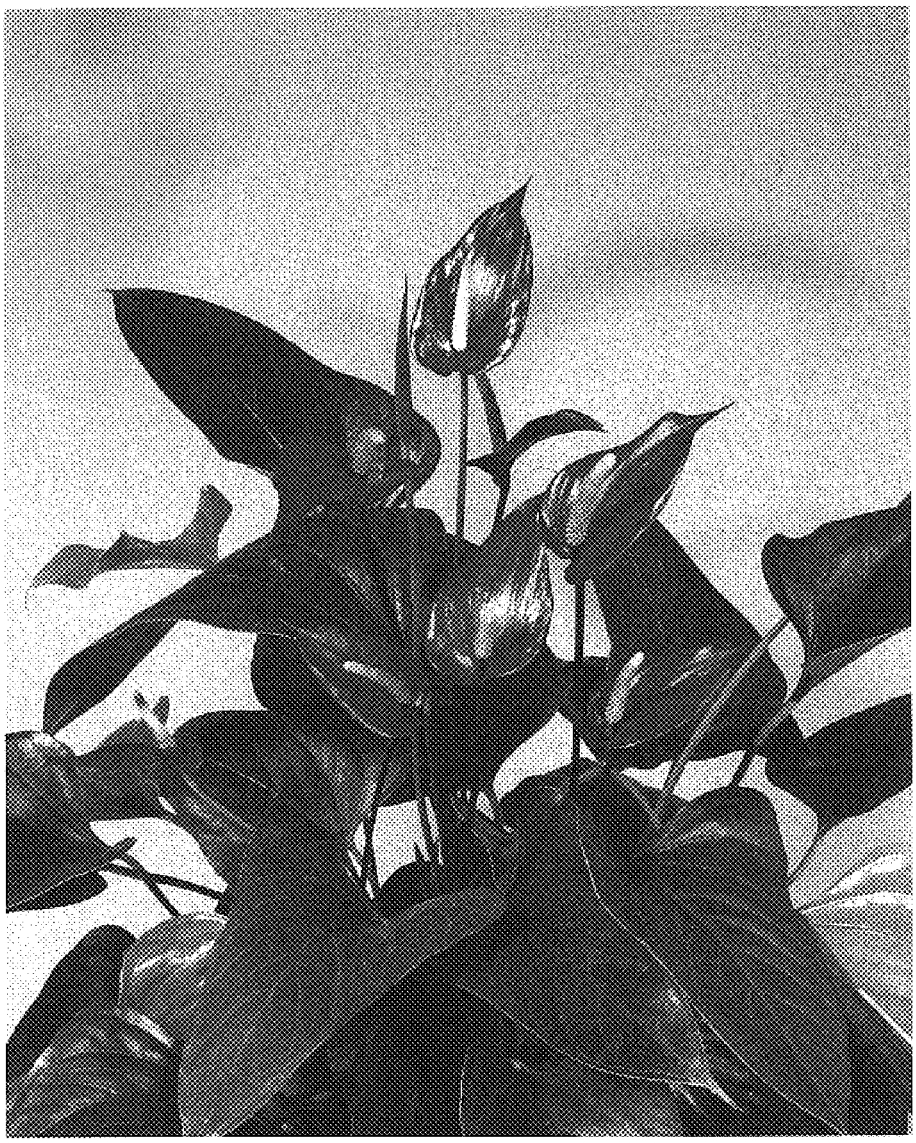

* * * * *